(12) United States Patent
Zhang

(10) Patent No.: US 10,071,404 B2
(45) Date of Patent: Sep. 11, 2018

(54) REFUSE TREATMENT METHOD AND APPARATUS FOR SEPARATING SOLID AND LIQUID AND SEPARATING ORGANICS AND INORGANICS

(71) Applicants: MISSISSIPPI INTERNATIONAL WATER INC., Valley Stream, NY (US); AMAZON ENVIRONMENTAL PROTECTION TECHNOLOGY AND EQUIPMENT PTE. LTD, Singapore (SG)

(72) Inventor: Dawei Zhang, Shenyang (CN)

(73) Assignees: MISSISSIPPI INTERNATIONAL WATER INC., Valley Stream, NY (US); AMAZON ENVIRONMENTAL PROTECTION TECHNOLOGY AND EQUIPMENT PTE. LTD., Singapore (SG)

( * ) Notice: Subject to any disclaimer, the term of this patent is extended or adjusted under 35 U.S.C. 154(b) by 243 days.

(21) Appl. No.: 15/033,253

(22) PCT Filed: Oct. 27, 2014

(86) PCT No.: PCT/CN2014/089559
§ 371 (c)(1),
(2) Date: Apr. 29, 2016

(87) PCT Pub. No.: WO2015/062458
PCT Pub. Date: May 7, 2015

(65) Prior Publication Data
US 2016/0243601 A1     Aug. 25, 2016

(30) Foreign Application Priority Data
Oct. 29, 2013   (CN) .......................... 2013 1 0519926

(51) Int. Cl.
*B09B 3/00*     (2006.01)
*B03B 9/06*     (2006.01)
(Continued)

(52) U.S. Cl.
CPC .................. *B09B 3/00* (2013.01); *B03B 9/06* (2013.01); *B09B 5/00* (2013.01); *C12M 21/04* (2013.01);
(Continued)

(58) Field of Classification Search
CPC ......... C12M 21/04; C12M 43/00; B09B 3/00; B09B 1/00; B09B 5/00; B03B 9/06;
(Continued)

(56) References Cited

FOREIGN PATENT DOCUMENTS

| CA | 2 783 179 A1 | 10/2004 |
|---|---|---|
| CN | 1328972 A | 1/2002 |

(Continued)

OTHER PUBLICATIONS

Yuanwe et al, Machine translation CN 102992559, pp. 1-9 (Year: 2013).*

(Continued)

*Primary Examiner* — Claire A Norris
(74) *Attorney, Agent, or Firm* — Merchant & Gould P.C.

(57) ABSTRACT

A refuse treatment method for separating solid and liquid and separating organics and inorganics, comprising the steps of: 1) subjecting municipal domestic refuse to a bag-breaking treatment and water washing; 2) washing the municipal domestic refuse after the bag-breaking treatment with water; 3) performing a solid liquid separation treatment on the washed municipal domestic refuse; 4) performing a cracking treatment and then a dehydration treatment on sorted water-insoluble organic refuse; 5) performing dehydration on marsh gas residue after marsh gas is generated in the refuse (Continued)

water to produce biochar. This application also discloses an apparatus for implementing the method described above.

9 Claims, 1 Drawing Sheet

(51) Int. Cl.
  *B09B 5/00* (2006.01)
  *C12M 1/107* (2006.01)
  *C12M 1/00* (2006.01)
  *F23G 5/027* (2006.01)
(52) U.S. Cl.
  CPC ............. *C12M 43/00* (2013.01); *F23G 5/027* (2013.01); *F23G 2201/30* (2013.01); *F23G 2900/50214* (2013.01); *Y02E 50/343* (2013.01); *Y02W 30/521* (2015.05)
(58) Field of Classification Search
  CPC .. C02F 11/04; C02F 11/10; C10G 2300/1003; C10J 2300/0946; B01D 3/009
  USPC ...... 210/603; 209/172, 172.5, 173; 241/24.1
  See application file for complete search history.

(56) References Cited

FOREIGN PATENT DOCUMENTS

| | | |
|---|---|---|
| CN | 101054212 A | 10/2007 |
| CN | 101073802 A | 11/2007 |
| CN | 101130194 B | 4/2010 |
| CN | 101716590 A | 6/2010 |
| CN | 201825737 U | 5/2011 |
| CN | 102503595 A | 6/2012 |
| CN | 102580982 A | 7/2012 |
| CN | 102896135 A | 1/2013 |
| CN | 102992559 A | 3/2013 |
| CN | 103286114 A | 9/2013 |
| CN | 103350028 A | 10/2013 |
| CN | 103599920 A | 2/2014 |
| JP | 2001-220274 A | 8/2001 |
| JP | 2005-313119 A | 11/2005 |
| JP | 2013-116439 A | 6/2013 |

OTHER PUBLICATIONS

Wu, Machine translation CN 1102503595, pp. 1-8 (Year: 2012).*
Extended European Search Report for corresponding European Patent Application No. 14858069.9 dated Aug. 17, 2017, 7 pages.
International Search Report for corresponding International Patent Application No. PCT/CN2014/089559 dated Jan. 14, 2015.
Chinese Office Action for corresponding Chinese Patent Application No. 201310519926.7 dated Feb. 2, 2015.

* cited by examiner

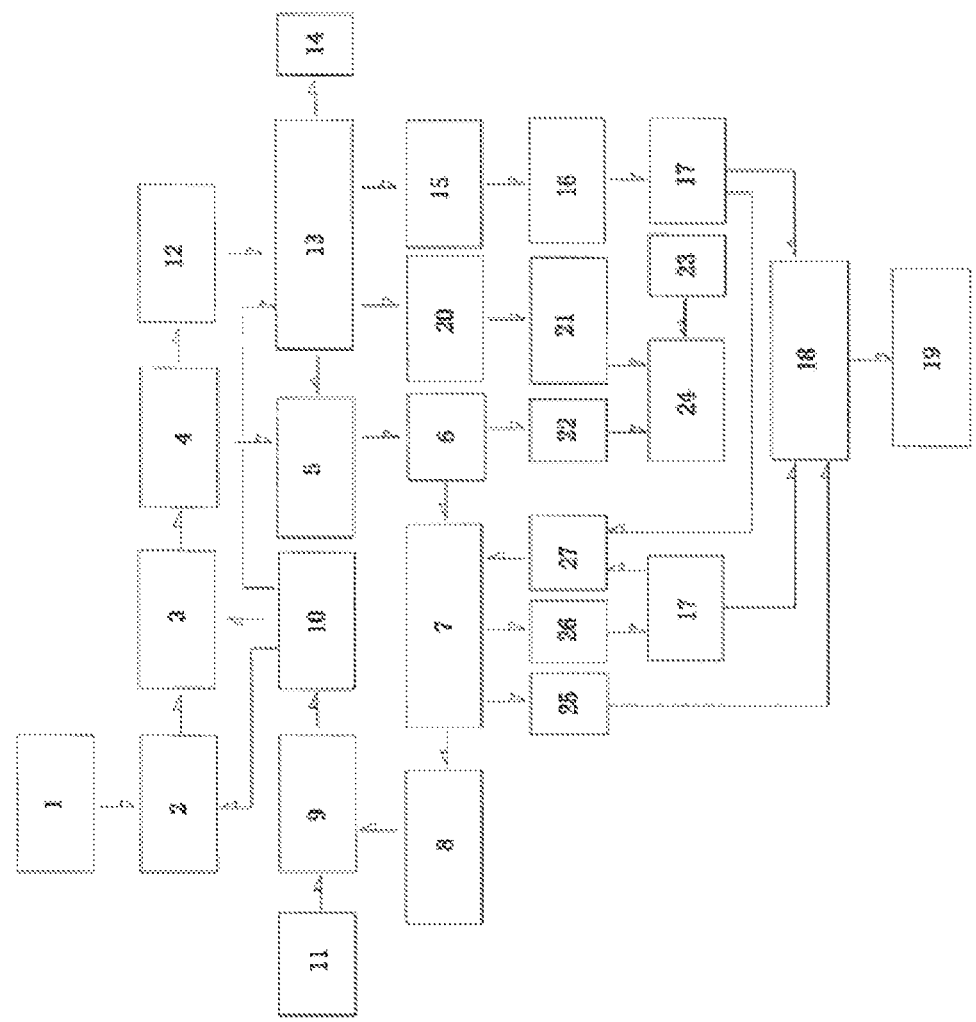

REFUSE TREATMENT METHOD AND APPARATUS FOR SEPARATING SOLID AND LIQUID AND SEPARATING ORGANICS AND INORGANICS

This application is a National Stage Application of PCT/CN2014/089559, filed 27 Oct. 2014, which claims benefit of Serial No. 201310519926.7, filed 29 Oct. 2013 in China and which applications are incorporated herein by reference. A claim of priority is made to each of the above disclosed applications.

TECHNICAL FIELD

This invention pertains to refuse treatment equipment, and in particular, relates to a refuse treatment method for separating solid and liquid and separating organics and inorganics.

This invention also relates to a refuse treatment apparatus for implementing the method described above.

BACKGROUND ART

China is one of the countries which have the most serious problems of municipal refuse.

According to statistics, the yield of municipal domestic refuse in the whole country was 115 million tons in 1980s, and had been 143 million tons in 1990s, which was the second in the world, next only to United States.

At present, the total amount of stockpiled municipal refuse in past years is up to 7 billion tons, and the amount of yield increases at a rate of about 8.98% per year. The stockpiled refuse occupies a total land area of up to 500 million square meters, which is converted to about 750 thousand mu of arable land.

70% of 600 large and middle cities in the whole country are surrounded by refuse, and the urban development and the living environment of surrounding residents are severely affected.

In our country, current refuse treatment substantially employs conventional methods such as landfill, composting, incineration, etc. However, the conventional refuse treatment techniques described above have well known defects.

I. Refuse Composting Treatment

The refuse composting treatment is a biochemical process which decomposes organic components in refuse using microorganisms. In the process of the biological chemical reaction, by means of the interaction of organics, oxygen and bacteria, carbon dioxide, water, and heat are emitted, and at the meanwhile, humus is generated.

The refuse composting treatment has the following three disadvantages.

1. Wastes, such as blocks, metal, glass, plastic, etc., cannot be decomposed by microorganisms, and these wastes must be sorted for further treatment;

2. The refuse composting has long period, large floor area, and poor sanitary conditions near refuse composting fields;

3. The compost has low efficiency, high cost, difficult selling, and poor economic benefit.

The refuse composting treatment is directed to organics capable of being decomposed by microorganisms, and thus it is a treatment technique only directed to organic components in refuse, not a final treatment technique for the entire refuse.

The refuse composting technique has the remarkable disadvantage that indecomposable organics and inorganics cannot be treated, and thus has low degrees of volume reduction, amount reduction, and harmlessness. Therefore, the problems of refuse cannot be thoroughly solved only by composting treatment. In some locations at present, domestic refuse is landfilled for nature fermentation, it is then excavated after several years, and sold as a fertilizer after indecomposable substances such plastic, etc., therein are screened out. Actually, this fertilizer is dangerous to plant fruit trees, vegetables, and crops for the reason that indecomposable organic components (paper, plastic, cloth, rubber, etc.) in refuse has a high content of heavy metals (Pb, Cd, Hg). If these substances are buried in the ground together with decomposable organics for a long term, along with the effect of rainwater, heavy metals will consequentially permeate final organic compost products, and foods produced using these composts will certainly have excessively high contents of heavy metals, which is harmful to the health of human.

II. Refuse Incineration Treatment

The refuse incineration is a process of delivering refuse to an incineration furnace for combustion. The thermal energy is released after the incineration of refuse, and flue gas and solid residue are generated at the meanwhile. The thermal energy needs to be recovered, the flue gas needs to be cleaned, and the residue needs to be digested. These are indispensable processes in the incineration treatment.

The refuse incineration treatment has the following disadvantages.

1. Toxic gases, such as dioxin, mercury vapor in batteries, etc., are released during refuse combustion. Flue gas generated must be cleaned, but the cleaning techniques are difficult and has high operation cost;

2. The process of refuse combustion generates toxic and harmful slag and dust, the amount of which is about 20%-30% of the original amount. The toxic and harmful slag and dust generated in incineration must also be treated.

3. It is a resource-wasting treatment method, as resources capable of being recovered and reutilized in refuse are destroyed 4. There are certain requirements for the low heat value of refuse in the incineration treatment, and not all types of refuse may be incinerated.

5. One-time investment for incineration equipment is high.

III. Refuse Landfill

The refuse landfill treatment has the following disadvantages.

The landfilled refuse does not subject to an innocent treatment, and a large amount of bacteria, viruses still remain; latent dangers such as marsh gas, pollution of heavy metals are hidden; and the effused liquid of refuse will pollute groundwater resources for a long time. Therefore, this method has extremely large potential dangers, and will bring out endless troubles to descendants. This method does not achieve reutilization treatment of refuse, but also occupies a large amount of land and leaves pollution sources to descendants. The most important is that the treatment capacity of each landfill field is limited and after filling, additional investment is still needed to construct a new landfill field, further occupying land resources. At present, refuse landfill is prohibited by official order in a number of developed countries.

Based on overall analysis, none of refuse treatment techniques used in our country at present is a method which can actually achieve the overall goals of refuse reutilization, innocuity, and amount reduction.

SUMMARY OF THE INVENTION

An object of this invention is to provide a refuse treatment method for separating solid and liquid and separating organics and inorganics.

Another object of this invention is to provide a refuse treatment apparatus for implementing the method described above.

To achieve the above objects, the present invention provides a refuse treatment method comprising the steps of:

1) subjecting municipal domestic refuse to a bag-breaking treatment and water washing;

2) performing a washing treatment on the municipal domestic refuse after the bag-breaking treatment with water to wash off water-soluble organics in the municipal domestic refuse;

3) performing a solid liquid separation treatment on the washed municipal domestic refuse, performing a sorting treatment on separated solid refuse, performing an anaerobic treatment on separated refuse water after precipitation to convert organics in the refuse water to marsh gas, and utilizing clear water after a cleaning treatment; and continuing to perform spray washing on the solid refuse in the sorting treatment, performing an anaerobic treatment on washed-off refuse water after precipitation to convert organics in the refuse water to marsh gas, and utilizing clear water after a cleaning treatment;

4) performing a cracking treatment and then a dehydration treatment on sorted water-insoluble organic refuse, performing a pyrolysis treatment in a hypoxic state to produce biochar, performing an anaerobic treatment on sewage generated during the dehydration treatment to convert organics in the sewage to marsh gas, and utilizing clear water after a cleaning treatment;

mixing sorted inorganic refuse subjected to cracking and silt precipitated from the refuse water for utilization; and directly recovering sorted plastics, metals, and batteries; and 5) performing dehydration on marsh gas residue after marsh gas is generated in the refuse water to produce biochar; and performing an anaerobic treatment on sewage generated during marsh gas residue dehydration and collecting the marsh gas generated in the anaerobic treatment for utilization.

In the refuse treatment method, the clear water after the cleaning treatment is cyclically used for washings in the processes of the bag-breaking treatment of refuse, the washing treatment of refuse, and the sorting treatment.

In the refuse treatment method, the generated marsh gas is used as a fuel for preparing biochar.

In the refuse treatment method, the produced biochar is used for producing a soil amendment.

In the refuse treatment method, particles of cracked inorganic refuse and the silt precipitated from the refuse water are mixed, and then cement is added to produce grass-planting bricks.

In the refuse treatment method, the biochar is produced from the marsh gas residue by performing carbonization in a hypoxic state.

The apparatus provided by this invention for implementing the refuse treatment method described above comprises the following configuration:

a refuse bag-breaking device is connected with a refuse washing device to wash off water-soluble organics in municipal domestic refuse;

the refuse washing device is connected with a solid liquid separation device to perform a solid liquid separation treatment on the washed municipal domestic refuse;

the solid liquid separation device is connected with a sorting device to perform a sorting treatment on separated solid refuse;

an organic refuse outlet provided in the sorting device is connected with a biochar-producing device, via an organic refuse cracking device and a dehydration device for performing dehydration on the organic refuse;

an inorganic refuse outlet provided in the sorting device is connected with an inorganic refuse cracking device;

a sewage outlet provided in the organic refuse dehydration device is connected with a refuse water anaerobic treatment device to perform an anaerobic treatment on separated sewage, so as to convert organics in the sewage to marsh gas;

the solid liquid separation device is connected with a sedimentation tank to precipitate the refuse water;

the sedimentation tank is connected with the refuse water anaerobic treatment device to perform an anaerobic treatment on separated refuse water after precipitation, so as to convert organics in the refuse water to marsh gas;

the refuse water anaerobic treatment device is connected with an activated coke filtration and adsorption device to perform a cleaning treatment on the refuse water after the anaerobic treatment by activated coke filtration and adsorption;

the activated coke filtration and adsorption device is connected with a circulating water tank;

the circulating water tank is connected with the refuse bag-breaking device, the refuse washing device, and the sorting device via a water circulating pump, such that the clear water after the cleaning treatment is cyclically used for washings in the processes of the bag-breaking treatment of refuse, the washing treatment of refuse, and the sorting treatment; and the refuse water anaerobic treatment device is provided with a marsh gas outlet, which is connected with the biochar-producing device.

In the apparatus, the refuse water anaerobic treatment device is connected with the biochar-producing device via a dehydration device for performing dehydration on marsh gas residue.

In the apparatus, the dehydration device for marsh gas residue is connected with the refuse water anaerobic treatment device via a sewage water outlet.

This invention has following characteristics.

(1) Overall treatment, comprising the separation treatment of solid and liquid in municipal domestic refuse; the separation treatment of inorganic refuse and organic refuse; and the cleaning treatment by washing refuse water for cyclic use, is achieved.

(2) Significant defects present in process techniques of conventional municipal domestic refuse treatments, such as defects of waste of land resources and pollution of groundwater resources present in refuse landfill treatment techniques; defects of air and environment pollution and waste of available resources present in refuse incineration treatment techniques, etc., are overcome.

(3) Available resources in municipal domestic refuse are allowed to be cleaned and recovered to the utmost extent.

(4) A large amount of valuable land resources are saved for cities.

(5) Air or environment pollution is not generated in the process of municipal domestic refuse treatment.

(6) Complete and thorough treatment of reutilization, innocuity, amount reduction, and low cost is achieved with respect to municipal domestic refuse treatment.

DESCRIPTION OF DRAWINGS

FIG. 1 is a process flow diagram of municipal domestic refuse treatment provided in an embodiment of this invention.

DESCRIPTION OF REFERENCE NUMERALS IN THE FIGURE

1: municipal domestic refuse; 2: refuse bag-breaking device; 3: refuse washing device; 4: solid liquid separation device; 5: refuse water; 6: sedimentation tank; 7: refuse water anaerobic treatment device; 8: activated coke filtration and adsorption device; 9: circulating water tank; 10: water circulating pump; 11: water supplement pipe; 12: solid refuse; 13: sorting device; 14: article such as plastic, metal, battery; 15: water-insoluble organic refuse; 16: organic refuse cracking device; 17: dehydration device; 18: biochar-producing device; 19: biochar; 20: inorganic refuse; 21: inorganic refuse cracking device; 22: silt; 23: cement; 24: grass-planting bricks; 25: marsh gas; 26: marsh gas residue; 27: sewage.

DESCRIPTION OF EMBODIMENTS

In order to enable objects, technical solutions, and advantages of this invention to be clearer, this invention will be further described in details in conjunction with the accompanying drawing.

This invention provides a treatment method and apparatus, which allow the separation treatment of solid and liquid in municipal domestic refuse, the separation treatment of inorganic refuse and organic refuse, and the cleaning treatment of refuse water for cyclic use, comprising:

1) washing treatment on municipal domestic refuse:

municipal domestic refuse after bag-breaking treatment is washed with clear water, so that (1) water-soluble organics in the municipal domestic refuse are washed off, avoiding liquid decay in the refuse, odor emission and environmental pollution in the process of refuse treatment; and (2) clean recovery of recoverable substances in the refuse is achieved;

2) cleaning treatment on refuse water after washing the refuse for cyclic use:

the refuse water after washing the refuse is transported to a solid liquid separation device for performing a solid liquid separation treatment and then is transported to a sedimentation tank; the refuse water after the treatment in the sedimentation tank is transported to a refuse water anaerobic treatment device for performing an anaerobic treatment to convert organics in the refuse water to marsh gas; the refuse water and marsh liquid discharged from the refuse water anaerobic treatment device are transported to an activated coke filtration and adsorption device for performing a cleaning treatment of filtration and adsorption; the clear water after the cleaning treatment of filtration and adsorption is transported to a circulating water tank, and water in the circulating water tank is transported via a water pump to a refuse washing device to be reused for refuse washing;

3) cleaning and sorting solid refuse after washing:

solid refuse separated from the solid liquid separation device is transported to a sorting device for performing a sorting treatment, and the refuse is continued to be cleaned in the sorting process of solid refuse; the refuse after the washing treatment is divided by the sorting device into recoverable refuse, water-insoluble organic refuse, and inorganic refuse, and the recoverable refuse is recovered;

4) producing sorted water-insoluble organic refuse into biochar and producing sorted inorganic refuse into grass-planting bricks and the like:

the sorted water-insoluble organic refuse is transported to an organic refuse cracking device for performing a cracking treatment and is then transported to a dehydration device for performing a dehydration treatment; the water-insoluble organic refuse after the dehydration treatment is transported to a carbonization biochar-producing device and is produced into biochar by performing a treatment in a hypoxic state; the produced biochar is used for producing a soil amendment; the inorganic refuse separated from the separation device is transported to an inorganic refuse cracking device; the particles of cracked inorganic refuse and the silt discharged from the sedimentation tank are mixed, and then cement is added to produce grass-planting bricks, etc.;

5) producing marsh gas residue in the process of refuse water treatment into biochar:

the marsh gas residue discharged from the refuse water anaerobic treatment device is transported to the dehydration device for performing a dehydration treatment, and is then transported to a carbonization biochar-producing device and is produced into biochar by performing a treatment in a hypoxic state; and 6) using marsh gas generated in the process of refuse water treatment as fuel of the carbonization biochar-producing device:

the marsh gas generated from the refuse water anaerobic treatment device is transported to the carbonization biochar-producing device, and is used as a fuel of the carbonization biochar-producing device for performing carbonization treatment on water-insoluble organic refuse and marsh gas residue to produce biochar.

The above overall treatment method and apparatus, which allow the separation treatment of solid and liquid in municipal domestic refuse, the separation treatment of inorganic refuse and organic refuse, and the cleaning treatment by washing refuse water for cyclic use, may avoid significant defects, such as waste of land resources and pollution of groundwater resources in conventional refuse landfill treatment techniques; air and environment pollution and waste of available resources in refuse incineration treatment techniques, etc., and really achieve the reutilization, innocuity, amount reduction, and cleaning treatment.

Preferred embodiments of this invention are described in details in conjunction with the accompanying drawing below. It is to be understood that preferred embodiments are provided to illustrate this invention but are not intended to limit the scope of this invention.

As shown in the figure, the treatment method and apparatus, which allow the separation treatment of solid and liquid in municipal domestic refuse, the separation treatment of inorganic refuse and organic refuse, and the cleaning treatment of refuse water for cyclic use, are as follows.

1. The municipal domestic refuse 1 is washed and the refuse water 5 is subjected to a cleaning treatment for cyclic use.

1) The municipal domestic refuse 1 is transported to a bag-breaking device 2 for performing a bag-breaking treatment and a spray washing is performed with water in the process of bag breaking. The refuse bag-breaking device 2 is a well-known equipment.

2) The municipal domestic refuse 1 after the bag-breaking treatment is transported to a refuse washing device 3 for performing a washing treatment with water to wash off water-soluble organics in the municipal domestic refuse 1. The refuse washing device 3 is a well-known equipment.

3) The washed municipal domestic refuse 1 is transported to a solid liquid separation device 4 for performing a solid liquid separation treatment. The solid liquid separation device 4 is a well-known equipment. The refuse water 5 after the solid liquid separation treatment is transported to a sedimentation tank 6. The refuse water 5 after the treatment in the sedimentation tank 6 is transported to a refuse water anaerobic treatment device 7 for performing an anaerobic treatment to convert organics in the refuse water 5 to marsh gas 25. The refuse water anaerobic treatment device 7 is a well-known equipment. The refuse water 5 after the anaerobic treatment is transported to an activated coke filtration and adsorption device 8 for performing a cleaning treatment. The activated coke filtration and adsorption device 8 is a well-known equipment, and "Refuse Water Treatment Device" (Patent No. ZL 2006 1 0011667.7, Publication No. CN 100496664C) may be used. The clear water after the cleaning treatment is transported to a circulating water tank 9, water in the circulating water tank 9 is transported to the refuse washing device 3, the refuse bag-breaking device 2, and a sorting device 13 via a water circulating pump 10 to be reused for refuse washing. The circulating water tank 9 is supplemented with water by a water supplement pipe 11.

2. The solid refuse 12 after washing is sorted and recovered for utilization.

Solid refuse 12 separated from the solid liquid separation device 4 is transported to a sorting device 13 for performing a sorting treatment, and the solid refuse 12 is continued to be subjected to spray washing in the process of sorting, with the washed-off refuse water 5 being transported to the sedimentation tank 6; articles 14, such as plastics, metals, batteries, etc., in the municipal domestic refuse 1 after the washing treatment is sorted out by the sorting device 13; and water-insoluble organic refuse 15 is transported to an organic refuse cracking device 16 for performing a cracking treatment and is then transported to a dehydration device 17 for performing a dehydration treatment. The organic refuse cracking device 16 is a well-known equipment. The water-insoluble organic refuse 15 after the dehydration treatment is transported to a biochar-producing device 18 and is produced into biochar 19 by performing a pyrolysis treatment in a hypoxic state. The biochar 19 is used for producing a soil amendment. The biochar producing device 18 is a well-known equipment, and "Device for producing biochar" (Patent No. ZL 2010 2 0562292.5, Publication No. CN201825737U) may be used. The dehydration device 17 dehydrates the cracked water-insoluble organic refuse 15, and the sewage 27 generated in this process is transported to the refuse water anaerobic treatment device 7 for treatment. The inorganic refuse 20 separated from the sorting device 13 is transported to an inorganic refuse cracking device 21, and the particles of cracked inorganic refuse 20 and the silt 22 discharged from the sedimentation tank 6 are mixed and then cement 23 is added to produce grass-planting bricks 24, etc.

3. Marsh gas 25 and marsh gas residue 26 generated in the treatment process of refuse water 5 are subjected to resource regeneration treatment and utilization.

The marsh gas residue 26 discharged from the refuse water anaerobic treatment device 7 is transported to a dehydration device 17; the marsh gas residue 26 after the dehydration treatment is transported to a biochar-producing device 18 and is produced into biochar 19 by performing a carbonization treatment in a hypoxic state. The biochar 19 is used for producing a soil amendment. The dehydration device 17 dehydrates the marsh gas residue 26, and the sewage 27 generated in this process is transported to the refuse water anaerobic treatment device 7 for treatment. The marsh gas 25 discharged from the refuse water anaerobic treatment device 7 is transported to the biochar producing device 18 and is used as a fuel for producing biochar 19 by performing carbonization treatment on the water-insoluble organic refuse 15 and the marsh gas residue 26.

The invention claimed is:

1. A refuse treatment method for separating solid and liquid and separating organics and inorganics, comprising the steps of:
    1) subjecting municipal domestic refuse to a bag-breaking treatment and water washing;
    2) performing a further washing treatment on the municipal domestic refuse after the bag-breaking treatment with water to wash off water-soluble organics in the municipal domestic refuse;
    3) performing a solid liquid separation treatment on the washed municipal domestic refuse; performing a sorting treatment on separated solid refuse; subjecting separated refuse water to sedimentation with a sedimentation tank; then performing an anaerobic treatment on the refuse water to convert organics in the refuse water to marsh gas; and performing a cleaning treatment on the refused water to obtain a clear water; and
    continuing to perform spray washing on the solid refuse in the sorting treatment, subjecting washed-off refuse water to sedimentation with a sedimentation tank, then performing an anaerobic treatment on the refuse water to convert organics in the refuse water to marsh gas, and performing a cleaning treatment on the refused water to obtain a clear water;
    4) performing a crushing treatment and then a dehydration treatment on sorted water-insoluble organic refuse obtained from step 3), performing a pyrolysis treatment in a hypoxic state to produce biochar, performing an anaerobic treatment on sewage generated during the dehydration treatment to convert organics in the sewage to marsh gas, and performing a cleaning treatment on the refused water to obtain a clear water;
    performing a crushing treatment on the sorted inorganic refuse obtained from step 3), and mixing the crushed inorganic refuse and silt sedimented from the refuse water; and
    directly recovering sorted plastics, metals, and batteries from the municipal domestic refuse; and
    5) performing a dehydration treatment on marsh gas residue after marsh gas is generated in the refuse water, and performing a pyrolysis treatment on the dehydrated mash gas residue in a hypoxic state to produce biochar; and performing an anaerobic treatment on sewage generated in the dehydration of the marsh gas residue to convert organics in the sewage to marsh gas, and collecting the marsh gas generated in the anaerobic treatment.

2. The refuse treatment method according to claim 1, further comprising cyclically using the clear water obtained from the cleaning treatment for washings in the processes of the bag-breaking treatment of refuse, the washing treatment of refuse, and the sorting treatment.

3. The refuse treatment method according to claim 1, wherein the generated marsh gas is used as a fuel for preparing biochar.

4. The refuse treatment method according to claim 1, wherein one or both of the biochar produced in step 4) and the biochar produced in step 5) are used for producing a soil amendment.

5. The refuse treatment method according to claim 1, wherein particles of crushed inorganic refuse and the silt sedimented from the refuse water are mixed, and then cement is added to produce grass-planting bricks.

6. The refuse treatment method according to claim 1, wherein the biochar is produced from the marsh gas residue by performing carbonization in a hypoxic state.

7. An apparatus for implementing the refuse treatment method of claim 1, wherein:
   a refuse bag-breaking device is connected with a refuse washing device to wash off water-soluble organics in municipal domestic refuse;
   the refuse washing device is connected with a solid liquid separation device to perform a solid liquid separation treatment on the washed municipal domestic refuse;
   the solid liquid separation device is connected with a sorting device to perform a sorting treatment on separated solid refuse;
   an organic refuse outlet provided in the sorting device is connected with a biochar-producing device, via an organic refuse crushing device and an organic refuse dehydration device;
   an inorganic refuse outlet provided in the sorting device is connected with an inorganic refuse crushing device;
   a sewage outlet provided in the organic refuse dehydration device is connected with a refuse water anaerobic treatment device to perform an anaerobic treatment on separated sewage to convert organics in the refuse water to marsh gas;
   the solid liquid separation device is connected with a sedimentation tank to subject the refuse water to sedimentation;
   the sedimentation tank is connected with the refuse water anaerobic treatment device to perform an anaerobic treatment on separated refuse water so as to convert organics in the refuse water to marsh gas after sedimentation;
   the refuse water anaerobic treatment device is connected with an activated coke filtration and adsorption device to perform a cleaning treatment on the refuse water after the anaerobic treatment by activated coke filtration and adsorption;
   the activated coke filtration and adsorption device is connected with a circulating water tank;
   the circulating water tank is connected with the refuse bag-breaking device, the refuse washing device, and the sorting device via a water circulating pump, such that a clear water obtained from the cleaning treatment is cyclically used for washings in the processes of the bag-breaking treatment of refuse, the washing treatment of refuse, and the sorting treatment; and
   the refuse water anaerobic treatment device is provided with a marsh gas outlet, which is connected with the biochar-producing device.

8. The apparatus according to claim 7, wherein the refuse water anaerobic treatment device is connected with the biochar-producing device via a marsh gas residue dehydration device.

9. The apparatus according to claim 8, wherein the marsh gas residue dehydration device is connected with the refuse water anaerobic treatment device via a refuse water outlet.

* * * * *